(12) United States Patent
Perez-Cruet et al.

(10) Patent No.: US 8,202,302 B2
(45) Date of Patent: Jun. 19, 2012

(54) PEDICLE SCREW AND ROD SYSTEM

(75) Inventors: Miguelangelo J. Perez-Cruet, Bloomfield, MI (US); John R. Pepper, Cheshire, CT (US)

(73) Assignee: MI4Spine, LLC, Bloomfield Hills, MI (US)

( * ) Notice: Subject to any disclaimer, the term of this patent is extended or adjusted under 35 U.S.C. 154(b) by 990 days.

(21) Appl. No.: 12/106,668

(22) Filed: Apr. 21, 2008

(65) Prior Publication Data
US 2008/0287994 A1 Nov. 20, 2008

Related U.S. Application Data

(60) Provisional application No. 60/912,872, filed on Apr. 19, 2007.

(51) Int. Cl.
*A61B 17/70* (2006.01)
(52) U.S. Cl. ........................................ 606/267; 606/271
(58) Field of Classification Search ............. 606/60–278
See application file for complete search history.

(56) References Cited

U.S. PATENT DOCUMENTS

| | | | | |
|---|---|---|---|---|
| 5,620,443 | A * | 4/1997 | Gertzbein et al. | 606/252 |
| 5,713,903 | A * | 2/1998 | Sander et al. | 606/326 |
| 6,224,598 | B1 * | 5/2001 | Jackson | 606/305 |
| 7,306,603 | B2 | 12/2007 | Boehm | |
| 7,524,323 | B2 * | 4/2009 | Malandain | 606/246 |
| 7,883,531 | B2 * | 2/2011 | de Coninck | 606/290 |
| 2004/0006342 | A1 * | 1/2004 | Altarac et al. | 606/61 |
| 2005/0085813 | A1 | 4/2005 | Spitler | |
| 2005/0245928 | A1 | 11/2005 | Colleran | |
| 2005/0277924 | A1 * | 12/2005 | Roychowdhury | 606/61 |
| 2006/0036240 | A1 | 2/2006 | Colleran | |
| 2006/0036244 | A1 | 2/2006 | Spitler | |
| 2006/0052784 | A1 * | 3/2006 | Dant et al. | 606/61 |
| 2006/0173454 | A1 | 8/2006 | Spitler | |
| 2008/0177332 | A1 * | 7/2008 | Reiley et al. | 606/301 |

OTHER PUBLICATIONS

IST Uncompromising, Motion/Lumbar, The Axient Total Dynamic Fixation System, Innovative Spinal Technologies, 2007.

* cited by examiner

*Primary Examiner* — Eduardo C Robert
*Assistant Examiner* — James Palmer
(74) *Attorney, Agent, or Firm* — John A. Miller; Miller IP Group, PLC

(57) ABSTRACT

A pedicle screw and rod system that has particular application for spinal fusion surgery. The system includes pedicle screws having ball-shaped heads that are threaded through pedicles of adjacent vertebra into the vertebral body. The system also includes two cannulated posts having a head portion with a planar portion and an opening for accepting the head of the pedicle screw in a secure and multi-axial engagement. The system further includes a tube portion that is coupled to the head portion and extends above the patient's skin. The system also includes a lordotic slotted rod that is slid down the tube portions to be positioned on top of the head portions of the posts so that the planar portions are locked within the slot. Bolts are then slid down the tube portions and are threaded to a threaded portion on the planar portion.

19 Claims, 3 Drawing Sheets

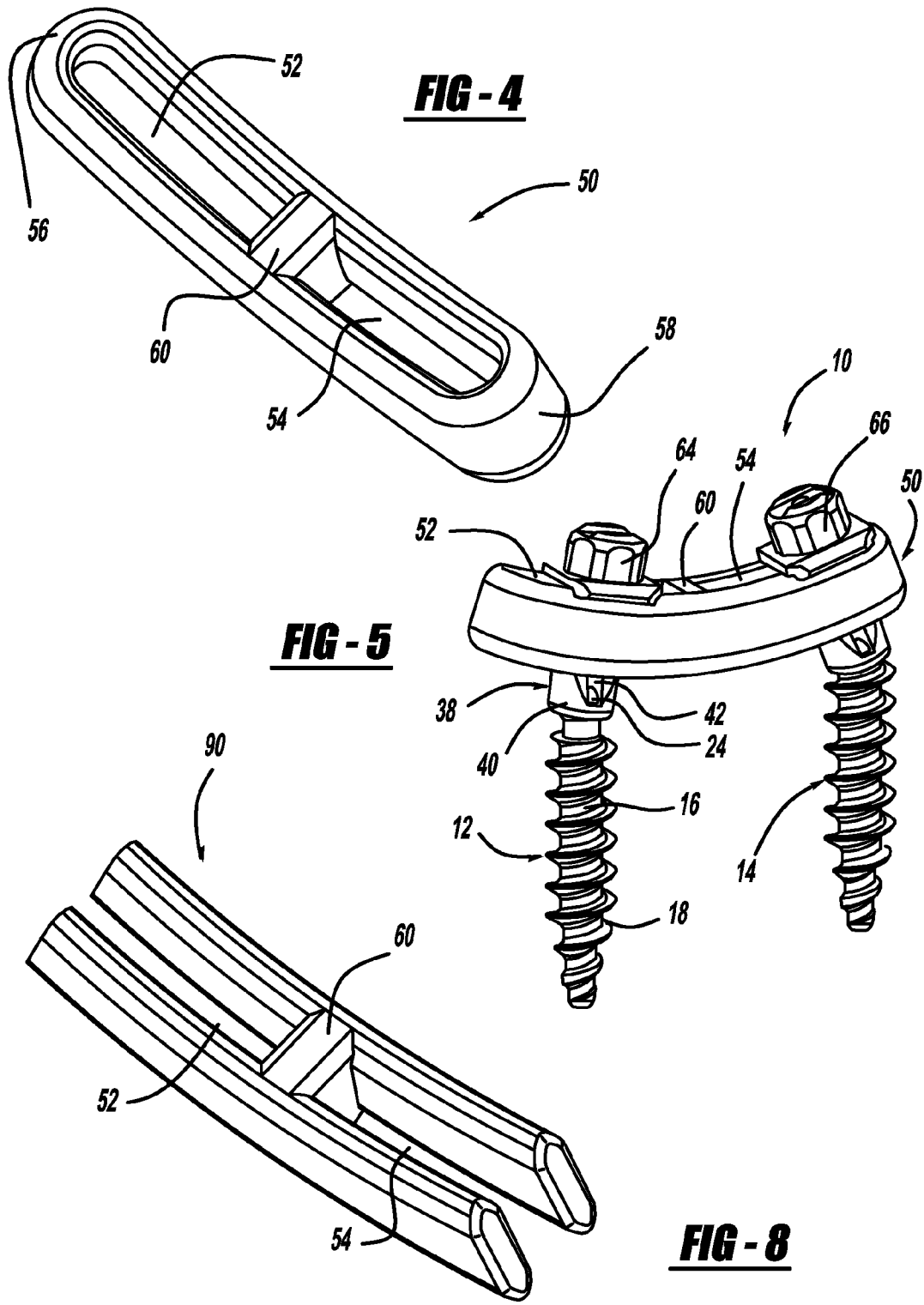

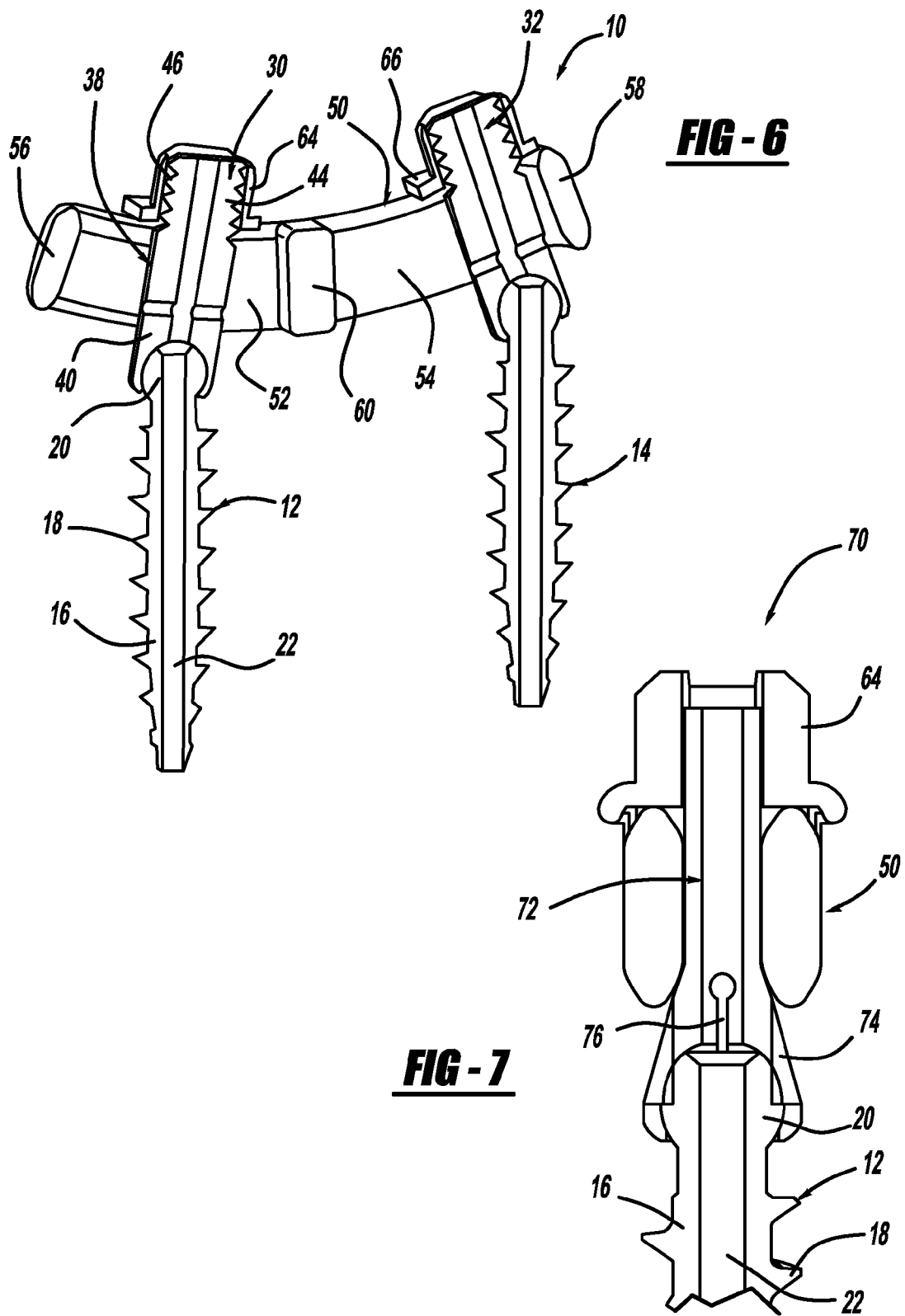

PEDICLE SCREW AND ROD SYSTEM

CROSS-REFERENCE TO RELATED APPLICATIONS

This application claims the benefit of priority to Provisional Patent Application Ser. No. 60/912,872, filed Apr. 19, 2007 and titled "Pedicle Screw and Rod System".

BACKGROUND OF THE INVENTION

1. Field of the Invention

This invention relates generally to a pedicle screw and rod system for spinal fusion surgery and, more particularly, to a pedicle screw and rod system for spinal fusion surgery where the rod includes a slot that holds a planar portion of a head of opposing post members.

2. Discussion of the Related Art

The human spine includes a series of vertebrae interconnected by connective tissue referred to as disks that act as a cushion between the vertebrae. The disks allow for movement of the vertebrae so that the back can bend and rotate.

Spinal fusion is a surgical procedure that fuses two or more vertebrae together using bone grafts and/or other devices. Spinal fusion is a commonly performed procedure for the treatment of chronic neck and back pain refractory to non-operative treatments. Spinal fusion is used to stabilize or eliminate motion of vertebrae segments that may be unstable, i.e., move in an abnormal way, that may lead to pain and discomfort. Spinal fusion is typically performed to treat injuries to the vertebrae, degeneration of the spinal disks, abnormal spinal curvature and a weak or unstable spine.

In an attempt to preserve normal anatomical structures during spine surgery, minimally invasive surgical procedures have been devised. One such procedure involves the use of a series of muscle dilators that separate the muscle fibers of the spine to create a pathway to the spine. A Kirschner (K-wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

Spinal fusion generally requires a graft material, usually bone material, to fuse the vertebrae together. The bone graft material can be placed over the spine to fuse adjacent vertebrae together. Alternatively, a cage is positioned between the vertebrae being fused, and is filed with the graft material. This procedure is referred to as interbody fusion since it is between adjacent vertebrae. The cage includes holes that allow the vertebrae and the graft material to grow together to provide the fusion. The cage supports the weight of adjacent vertebrae while the fusion is occurring through the cage. Alternatively, the bone graft material can be placed directly over or lateral to the spine, referred to as postero-lateral fusion. Typically the bone graft material is autogenous bone material taken from the patient, or allograft bone material harvested from cadavers. Synthetic bone materials can also be used as the graft material. Generally, the patient's own bone material offers the best fusion material and is the current "gold standard".

Spinal instrumentation is then performed to immobilize the vertebral segments where the bone is placed. Similar to the function of wearing a cast or brace after breaking a long bone, spinal instrumentation allows for immobilization, which promotes bone fusion. One of the most common forms of spinal instrumentation is the pedicle screw and rod construct. The rods, which span adjacent vertebrae, are mounted to the vertebra using pedicle screws that are threaded through the pedicles of each vertebra and into the vertebral body. Accurate placement of the pedicle screws relative to the vertebral pedicle is very important to prevent injury to nerves or spinal cord. Typically, fluoroscopy is used to ensure that the pedicle screws are properly oriented relative to the pedicle.

In traditional open pedicle screw instrumentation, the muscles are stripped off the bony anatomy of the spine to expose the facet and transverse process for accurate pedicle screw placement. This results in significant muscle and ligamentous damage resulting in significant post-operative pain and discomfort for patients and often extending hospital stays. Recovery times can be extended and additional problems at adjacent levels of the spine can ultimately result in more surgery.

Recently, minimally invasive spine instrumentation techniques have been developed to perform percutaneous pedicle screw instrumentation. In this procedure, pedicle screws and rods can be placed without stripping the muscles and ligaments off the spine This results in significant recovery benefits for patients undergoing spine fusion and instrumentation. Since the normal anatomical integrity of the spine is maintained, long-term spine health is improved.

In one known process of percutaneous pedicle screw instrumentation, a Jamshidi needle is used to dock on to the junction of the vertebrae between the facet complex and the transverse process of the vertebra. Gentle taps with a mallet cause the Jamshidi needle to be advanced through the pedicle, making sure not to cross the medial border of the pedicle, which can result in nerve root injury, until the junction between the pedicle base and the vertebral body is reached. Fluoroscopic visualization into the anterior posterior and lateral planes of the vertebra is used to see the orientation of the Jamshidi needle. The correct trajectory of the Jamshidi needle should place the tip of the needle in the center of the pedicle in the anterior posterior view when the tip of the Jamshidi needle lies at the pedicle vertebral body junction in the lateral view.

Once the junction between the base of the pedicle wall and the vertebral body is reached, the Jamshidi needle can be directed in a more medial fashion. The Jamshidi needle is typically passed to about one-half the depth of the vertebral body, and then a K-wire is passed down the Jamshidi needle and into the vertebral body a little farther to seat it into the bone. The Jamshidi needle is then removed. A series of canulated muscle dilators are then passed over the K-wire to prevent the soft tissue from going into the threads of the tap and a pedicle screw is then passed down the dilators. The pedicle is tapped and the appropriate size pedicle screw is placed.

SUMMARY OF THE INVENTION

In accordance with the teachings of the present invention, a pedicle screw and rod system is disclosed that has particular application for spinal fusion surgery. The system includes pedicle screws having ball-shaped heads that are threaded through pedicles of adjacent vertebra into the vertebral body. The system also includes two cannulated posts having a head portion with a planar portion and an opening for accepting the head of the pedicle screw in a secure and multi-axial engagement. The system further includes a tube portion that is coupled to the head portion and extends above the patient's skin. The system also includes a lordotic slotted rod that is slid down the tube portions to be positioned on top of the head portions of the posts so that the planar portions are locked within the slot. Bolts are then slid down the tube portions and are threaded to a threaded portion on the planar portion. A weakened portion of the tube portion is provided just above the head portion, so that when the post is properly torqued, the tube portion will break at the weakened portion, and can be removed from the patient.

Additional features of the present invention will become apparent from the following description and appended claims, taken in conjunction with the accompanying drawings.

BRIEF DESCRIPTION OF THE DRAWINGS

FIG. 4 is a perspective view of a slotted rod used in the system shown in FIG. 1;

FIG. 5 is a perspective view of the pedicle screw and rod system shown in FIG. 1 where bolts have been secured to the tube heads and the tubes have been broken off;

FIG. 6 is a cross-sectional view of the pedicle screw and rod system shown in FIG. 5;

FIG. 7 is a cross-sectional view of a pedicle screw and rod system, according to another embodiment of the invention; and FIG. 8 is a perspective view of an open-ended rod for a pedicle screw and rod system, according to another embodiment of the present invention.

DETAILED DESCRIPTION OF THE EMBODIMENTS

The following discussion of the embodiments of the invention directed to a pedicle screw and rod system for spinal fusion surgery is merely exemplary in nature, and is in no way intended to limit the invention or its applications or uses. For example, the pedicle screw and rod system of the invention has particular application for spinal fusion surgery. However, the pedicle screw system of the invention may have other applications.

Figure 1:
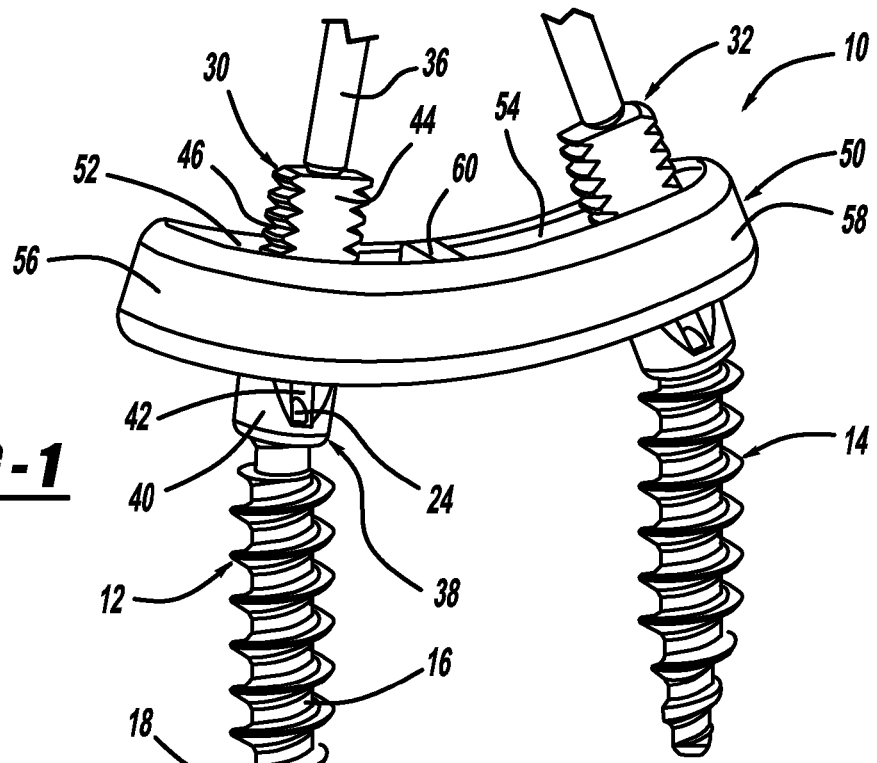
FIG. 1 is a perspective view of a pedicle screw and a rod system, according to an embodiment of the present invention.
Figure 2:
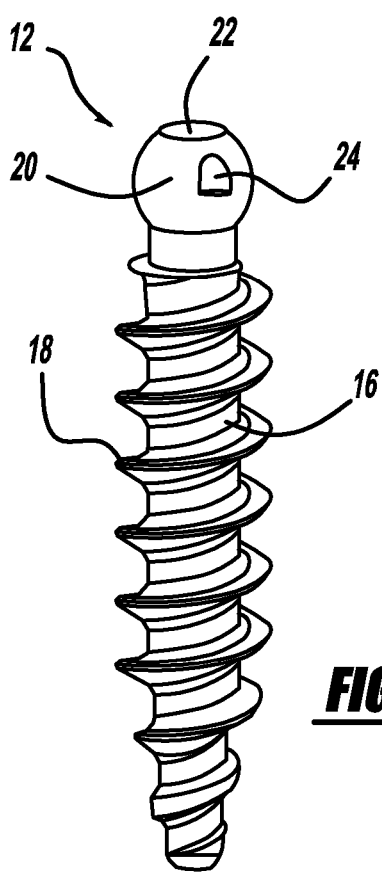
FIG. 2 is a perspective view of one of the pedicle screws used in the system shown in FIG. 1.

FIG. 1 is a perspective view of a pedicle screw and rod system 10, according to an embodiment of the present invention. The system 10 includes a pair of pedicle screws 12 and 14, where a perspective view of the pedicle screw 12 is shown in FIG. 2. The pedicle screw 12 includes a body portion 16 having outer threads 18 and a ball-shaped head 20. A channel 22 extends through the head 20 and the body portion 16 making the pedicle screw cannulated. A pair of opposing tabs 24 is formed to the head 20 for reasons that will become apparent from the discussion below.

Figure 3:
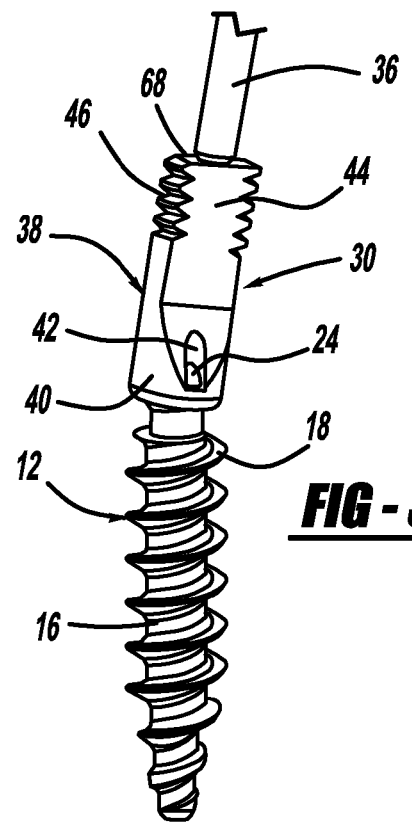
FIG. 3 is a perspective view of one of the pedicle screws and a cannulated tube associated with the system shown in FIG. 1.

A cannulated post 30 is mounted to the pedicle screw 12 and a cannulated post 32 is mounted to the pedicle screw 14. FIG. 3 is a perspective view of the pedicle screw 12 and the cannulated post 30 separated from the system 10. The cannulated post 30 includes a tube portion 36 and a head portion 38. The head portion 38 includes a flared end portion 40 having a cup opening that is configured to accept the head 20 of the pedicle screw 12 so that the post 30 can rotate multi-axially relative thereto. The end portion 40 includes a slot 42 in which the tab 24 is positioned so as to lock the cannulated post 30 to the pedicle screw 12 in a snap fit. Particularly, the cup opening in the end portion 40 is forced on to the head 20 in a tight engagement so that when the slot 42 reaches the tab 24, the post 30 is snapped onto the pedicle screw 12 in a secure manner.

The head portion 38 also includes a planar portion 44 having external threads 46 along its edges and opposing flat surfaces for reasons that will become apparent from the discussion below.

The system 10 includes a lordotic rod 50 that couples the screws 12 and 14 together. FIG. 4 is a perspective view of the rod 50 removed from the system 10. The rod 50 includes aligned slots 52 and 54 that extend from one end 56 to the other end 58 of the rod 50, and are separated by a transverse center bar 60 that provides rigidity and support. The rod 50 is lordotic in that it has an angle that matches the curvature of a patient's spine, particularly the lumbar spine.

Once the pedicle screws 12 and 14 have been mounted to adjacent vertebrae, the posts 30 and 32 are snapped onto the heads of the screws. The rod 50 is slid down the tube portion 36 so that the planar portions 44 of the head portions 38 of the posts 30 and 32 are positioned within the slots 52 and 54 on both sides of the bar 60, as shown. Thus, the rod 50 is locked to the posts 30 and 32.

FIG. 5 is a perspective view and FIG. 6 is a cross-sectional view of the system 10. Once the rod 50 is in place on the head portions 38, a bolt 64 is slid down the tube portion 36 and is threaded to the threads 46 to hold the post 30 and the screw 12 to the rod 50. Likewise, a bolt 66 is slid down the tube of the cannulated post 32 and is threaded to the threaded portion of the post 32. Once the bolts 64 and 66 are in place, the tube portion 36 is broken away from the head portion 38 at a weakened joint 68 therebetween, and the tube portion of the rod 32 is broken away from the head portion of the post 32.

FIG. 7 is a cross-sectional view of a pedicle screw and rod system 70, where like elements to the system 10 are shown by the same reference numeral, according to another embodiment of the present invention. In this embodiment, the head portion 38 of the post 30 is replaced with a head portion 72 that includes a flared end 74. A slot 76 extends through a sidewall of the flared end 74, as shown, and allows the flared end 74 to separate when being pushed onto the head 20 of the screw 12, and to snap in place and be rigidly secured thereto.

FIG. 8 is a perspective view of a lordotic rod 90 similar to the lordotic rod 50, where like elements are identified by the same reference numeral. The lordotic rod 90 has the end sections 54 and 56 removed so that the head portions 38 of the posts 30 and 32 can be more easily slid into the slots 52 and 54.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A pedicle screw and rod system comprising:
    a pedicle screw including a body and a ball-shaped head;
    a cannulated post including a tube portion and a head portion attached thereto, said head portion including an opening that accepts the ball-shaped head of the pedicle screw in a multi-axial engagement, said head portion further including a planar portion having external threads; and a rod having a slot that accepts the head portion of the cannulated post where the planar portion of the head portion causes the post to be locked within the slot, wherein the cannulated post extends through the slot to allow the head portion of the post to be positioned within the slot, wherein the ball-shaped head of the pedicle screw includes opposing tabs that snap fit into opposing slots in the opening of the head portion of the post.

2. The system according to claim 1 further comprising a bolt threaded to the head portion to secure the pedicle screw to the rod.

3. The system according to claim 1 wherein the tube portion of the cannulated post has a weakened portion where it is coupled to the head portion so that tube portion can be broken away from the head portion.

4. The system according to claim 1 wherein the rod is a lordotic rod.

5. The system according to claim 1 wherein the rod includes a transverse bar extending across the slot.

6. The system according to claim 1 wherein the rod includes open end portions.

7. The system according to claim 1 wherein the planar portion of the head portion includes opposing flat surfaces.

8. A pedicle screw and rod system comprising:
   first and second pedicle screws each including a body and a ball-shaped head;
   first and second cannulated posts each including a tube portion and a head portion attached thereto where the head portion of the first cannulated post includes an opening that accepts the ball-shaped head of the first pedicle screw in a multi-axial engagement and the head portion of the second cannulated post includes an opening that accepts the ball-shaped head of the second pedicle screw in a multi-axial engagement, said head portion of each cannulated post further including a planar portion having external threads; and
   a rod including a slot, said rod being operable to extend down the first and second cannulated post so that the tube portions slide through the slot and the head portions of the first and second cannulated posts are positioned within the slot where the planar portion of the head portions cause the first and second cannulated posts to be locked within the rod, wherein the ball-shaped head portions of the pedicle screws include opposing tabs that snap fit into opposing slots in the opening of the head portions of the posts.

9. The system according to claim 8 further comprising a first bolt threaded to the head portion of the first cannulated post to secure the first pedicle screw to the rod and a second bolt threaded to the head portion of the second cannulated post to secure the second pedicle screw to the rod.

10. The system according to claim 8 wherein the tube portions of the cannulated posts have a weakened portion where they are coupled to the head portions so that tube portions can be easily broken away from the head portions.

11. The system according to claim 8 wherein the rod is a lordotic rod.

12. The system according to claim 8 wherein the rod includes a transverse bar extending across the slot.

13. The system according to claim 8 wherein the rod includes open end portions.

14. The system according to claim 8 wherein the planar portion of the head portion includes opposing flat surfaces.

15. A pedicle screw and rod system comprising:
   a pedicle screw including a body and a ball-shaped head;
   a cannulated post including a tube portion and a head portion attached thereto, said head portion including an opening that accepts the ball-shaped head of the pedicle screw in a multi-axial engagement, said head portion further including a planar portion having external threads, wherein the tube portion of the cannulated post has a weakened portion where it is coupled to the head portion so that tube portion can be broken away from the head portion;
   a rod having a slot that accepts the head portion of the cannulated post where the planar portion of the head portion causes the post to be locked within the slot, wherein the cannulated post extends through the slot to allow the head portion of the post to be positioned within the slot, wherein the ball-shaped head of the pedicle screw includes opposing tabs that snap fit into opposing slots in the opening of the head portion of the post; and
   a bolt threaded to the head portion to secure the pedicle screw to the rod.

16. The system according to claim 15 wherein the rod is a lordotic rod.

17. The system according to claim 15 wherein the rod includes a transverse bar extending across the slot.

18. The system according to claim 15 wherein the rod includes open end portions.

19. The system according to claim 15 wherein the planar portion of the head portion includes opposing flat surfaces.

* * * * *